United States Patent
Rao et al.

(10) Patent No.: US 10,125,383 B2
(45) Date of Patent: Nov. 13, 2018

(54) **METHOD FOR PRODUCING L-CITRULLINE BY USING A RECOMBINANT *CORYNEBACTERIUM CRENATUM* STRAIN**

(71) Applicants: Zhiming Rao, Wuxi (CN); Meizhou Wang, Wuxi (CN); Meijuan Xu, Wuxi (CN); Xian Zhang, Wuxi (CN); Taowei Yang, Wuxi (CN)

(72) Inventors: Zhiming Rao, Wuxi (CN); Meizhou Wang, Wuxi (CN); Meijuan Xu, Wuxi (CN); Xian Zhang, Wuxi (CN); Taowei Yang, Wuxi (CN)

(73) Assignee: Jiangnan University, Wuxi, JS (CN)

( * ) Notice: Subject to any disclaimer, the term of this patent is extended or adjusted under 35 U.S.C. 154(b) by 0 days.

(21) Appl. No.: 15/876,478

(22) Filed: Jan. 22, 2018

(65) Prior Publication Data

US 2018/0148749 A1 May 31, 2018

Related U.S. Application Data

(63) Continuation of application No. PCT/CN2015/096672, filed on Dec. 8, 2015.

(30) Foreign Application Priority Data

Oct. 28, 2015 (CN) .......................... 2015 1 0712520

(51) Int. Cl.
*C12P 13/10* (2006.01)
*C12N 15/77* (2006.01)
*C12N 9/78* (2006.01)
*C12R 1/15* (2006.01)

(52) U.S. Cl.
CPC ................ *C12P 13/10* (2013.01); *C12N 9/78* (2013.01); *C12N 15/77* (2013.01); *C12Y 305/03006* (2013.01); *C12R 1/15* (2013.01)

(58) Field of Classification Search
CPC ....................................................... C12P 13/10
USPC ......................................................... 435/114
See application file for complete search history.

(56) References Cited

FOREIGN PATENT DOCUMENTS

CN 201510712520 * 10/2015 .............. C12P 13/10

* cited by examiner

*Primary Examiner* — Tekchand Saidha
(74) *Attorney, Agent, or Firm* — Lili Chen

(57) ABSTRACT

Disclosed is a method for producing L-citrulline using recombinant *Corynebacterium crenatum* cells as whole-cell biocatalysts. The present invention provides a recombinant *C. crenatum* that expresses an exogenous arginine deiminase gene from *Lactobacillus brevis*. The recombinant *C. crenatum* SDNN403 is used as biocatalysts for converting L-arginine to produce L-citrulline. Using the method of the invention, the concentration of L-citrulline reached 301.4 g/L after a 48 hr conversion reaction, and the molar conversion rate reached 99.9%.

9 Claims, No Drawings
Specification includes a Sequence Listing.

SEQUENCE LISTING

<160> NUMBER OF SEQ ID NOS: 3

<210> SEQ ID NO 1
<211> LENGTH: 1233
<212> TYPE: DNA

```
<213> ORGANISM: Lactobacillus brevis

<400> SEQUENCE: 1
atgacaagtc cgattcacgt aatgtccgaa attggtaagt taaagacggt aatgctcaag      60
cggccgaacg ttgaagtgga aaacttcacg cctgatatga tggaacgcct gctgtttgat     120
gacattccat atttaccaat tgcgcaacaa gaacatgata actttgctga aactttacgg     180
caaaacggta cggaagtctt gtatttggaa caactctctg ccgaagccct cgatgacggt     240
ggcgaagagg ttaagttaaa cttcctggaa caaatgcttg ctgaaagtgg ctacgttgct     300
ggtgtaacgc atgacgcttt gaaagaatac ttattatcat tggatacccca agccatggtc    360 aacaagatta tgggtggtgt acggaagaat gagctcgact ttgtcccagc tgatttggtc    420
agtgcggctg aagaagacga ttatccattc tttatggatc caatgcctaa cttatacttt    480
acgcgagatc ctgccgcttc aatcggtgat gggttgagta tcaaccatat gaccttcgcc    540
gctcggcaac gtgaatcact ctttatggaa acaatcatca agtatcatca tcgatttgct    600
aacaagggtc tcaatgtttg gcgtgaccga aaccatgata cacgaatcga aggtggggac    660
gaattagtct tatccgatca tgtcttggca attggggttt ctcaacggac ctctgctgat    720
gcgattgaag acattgcccg taacctgttt gccaagagtc attttgacaa ggttattgcc    780
attaagattc cacataacca tgccatgatg catttggaca cggtcttcac gatgattaac    840
accgaccaat tcacggttca cccaggtatc ttaggtgaag gtggtcatat cgatacttgg    900
acgattacgc caggtaaaga tggtcaatta agccttgatc accaaacaga tttgaagaag    960
gtcttgaagg atgctttgaa ccttgacgat ttagatttga ttccaacggg taacggcgat   1020
ccaatcattg ctggccgtga acaatggaat gacggctcca atactttggc aattgcacct   1080
ggtgttgtag ttacttacaa ccggaattac gtttccaatg aattattacg taagcatggt   1140
ctaaaagtga ttgatgtctt atcaagtgaa ttgtcacggg gccgtggcgg tcctcgttgc   1200
atgagtatgc cattagttcg agaagacctt taa                                1233

<210> SEQ ID NO 2
<211> LENGTH: 35
<212> TYPE: DNA
<213> ORGANISM: Artificial Sequence
<220> FEATURE:
<223> OTHER INFORMATION: DNA Primer

<400> SEQUENCE: 2
acccgaagct tatgacaagt ccgattcacg taatg                                35

<210> SEQ ID NO 3
<211> LENGTH: 35
<212> TYPE: DNA
<213> ORGANISM: Artificial Sequence
<220> FEATURE:
<223> OTHER INFORMATION: DNA Primer

<400> SEQUENCE: 3
accggaattc ttaaaggtct tctcgaacta atggc                                35
```

METHOD FOR PRODUCING L-CITRULLINE BY USING A RECOMBINANT *CORYNEBACTERIUM CRENATUM* STRAIN

CROSS-REFERENCES AND RELATED APPLICATIONS

This application is a continuation application of international application PCT/CN2015/096672, entitled "A Method for Producing L-Citrulline by Using a Recombinant *Corynebacterium crenatum* Strain", filed Dec. 8, 2015, which claims the priority to Chinese patent application No. 201510712520.X, filed Oct. 28, 2015, the contents of which are herein incorporated by reference in entirety.

BACKGROUND OF THE INVENTION

Field of the Invention

The present invention relates to the field of biological engineering and biotechnology. In particular, it relates to methods for producing L-citrulline using engineered microorganisms.

Description of the Related Art

L-arginine deiminase (Argininedeiminase, E.0 .3.5.3.6, ADI), a key enzyme of microorganism arginine metabolism pathway, catalyzes L-arginine and transforms it to L-citrulline and ammonia. ADI is widely present in *Bacillus cereus, Streptococcus faecalis, Pseudomonas* and *mycoplasma* microorganisms (e.g. malodors). It has been found that ADI could inhibit animal vascular endothelial cell proliferation and various types of malignancies proliferation. ADI purified from *Mycoplasma arginine* inhibits cell migration of several types of cancer cells in human body. In addition, ADI could directly control the growth of tumor cells by suppressing the synthesis of biogenic amine. Therefore, arginine deiminase as a novel anti-tumor substance has attracted attention in the field of medicine. The ADI also could be employed to the industrial production of citrulline because it can hydrolyze arginine to produce citrulline.

L-citrulline is an important non-protein amino acid, which is an important intermediate metabolite of urea cycle in a human body. It not only functions as an antioxidant by absorbing and removing harmful free radicals, but also effectively protects the DNA and PMN from oxidative reactions through increasing the arginine required for NO synthesis. In addition, it can be used as anti-aging products and health care products for improving immunity. It can also be used as anti-wrinkle and anti-aging skin care products. In the field of medicine, L-citrulline can be used to treat prostate diseases, especially for prostatitis and prostate cancer because L-citrulline enables human body to produce nitrogen oxides, which is a very important substance for male potency. Recently, studies have shown that the conversion of citrulline to L-arginine in human bodies plays an important role in maintaining the normal function of cardiovascular nitric oxide metabolism.

Methods for L-citrulline industrial production include chemical synthesis, natural extraction, microbial fermentation and L-arginine hydrolysis.

High titer strains for L-citrulline production with microbial fermentation was primarily obtained through mutagenesis or genetic engineering methods, and those strains can produce L-citrulline from cheap starting materials such as glucose and starch. These types of research started in Japan from 1930s and reached to a relatively high level in 1960s. Kyowa Hakko Kogyo Company found an *Arthrobacter paraffineus* that produced citrulline from hydrocarbon. It utilized 1% $NH_4NO_3$ and 0.5% yeast extract as nitrogen source combined with 1 mg/L $VB_1$ and other ingredients, and produced 7.1g /L citrulline after 96 h fermentation. This method has disadvantages of low efficiency and long fermentation period, not suitable for L-citrulline industrial production.

Methods of L-arginine hydrolysis include alkaline hydrolysis and enzymatic hydrolysis. The method of enzymatic hydrolysis has the advantages of having higher yields, few purification steps, and few D-type optical rotation enantiomers in the final product, simple production process and low cost of the production. Ichiron Chibata reported that strains including *Psudomonas putida* ATCC 4359, *Pseudomonas fluorescen* IFO 30081, *Pseudomonas ovalis* IAM 1002, and *Leuconostoc citrovorum* ATCC 8081 produces ADI and can converse L-arginine or DL-arginine to 80 g/L citrulline. Other research has been found that 92.72g/L citrulline can be produced from arginine by *Streptococcus faecalis* within 25 hours. However, those methods are still far away from meeting the needs of industrial production.

SUMMARY OF THE INVENTION

The first goal of the present invention is to provide a recombinant strain with expression of arginine deiminase, which is carried out by ligating an arginine deiminase gene arcA to pXMJ19 and then transfers the expression vector pXMJ19-arcA to *Corynebacterium crenatum* (*C. crenatum*) SDNN403 to obtain a genetically engineered *C. crenatum* SDNN403/pXMJ19-arcA.

In one embodiment of the present invention, the *C.crenatum* SDNN403 was deposited in China General Microbiological Culture Collection Center with the accession number of CGMCC No. 0890.

In one embodiment of the present invention, the arginine deiminase gene with the sequence of SEQ ID NO: 1 is derived from *Lactobacillus brevis*.

The second goal of the present invention is to provide a method for L-citrulline production using whole-cell biocatalysts.

In one embodiment of the present invention, the method is carried out in a reaction system using L-arginine as the substrate, the genetically engineered stain as the whole-cell catalyst.

In one embodiment of the present invention, the reaction system is a phosphate buffer at pH 6.0-7.0.

In one embodiment of the present invention, the concentration of free whole-cell is at OD600=7-8, and the concentration of L-arginine is 80-100 g/L.

In one embodiment of the present invention, the temperature of the whole-cell catalyst is under 40-45° C.

In one embodiment of the present invention, L-arginine is supplemented into the reaction system to maintain a concentration at 60-100 g/L.

In one embodiment of the present invention, the reaction system contains 1.0 mM $Mn^{2+}$ and/or 1.0 mM $Mg^{2+}$.

In one embodiment of the present invention, the citrulline conversion is performed in pH 6.4 phosphate buffer, added with 100 g/L arginine, 1.0 mM $Mn^{2+}$, 1.0 mM $Mg^{2+}$; the conversion process is under 40-45° C., the concentration of arginine is maintained at 60-100 g/L by supplementing arginine into the reaction system.

The advantages of the present invention include: (1) the present invention provides an genetically engineered strain *C. crenatum* SDNN403/pXMJ19-arcA that produces arginine deiminase with 2.56 U/mg enzyme activity; (2) The present invention provides a method for L-citrulline production from arginine conversion using the recombinant strain *C. crenatum* SDNN403/pXMJ19-arcA, which achieves a citrulline tilter of 301.4 g/L after 48 hour conversion reaction. The conversion rate from arginine to citrulline reaches 99.9%. Compared with the existing methods for producing L-citrulline by enzymatic conversion, the production efficiency and the yield have been greatly improved. The method of the present invention also has the advantages of strong product specificity, high conversion efficiency, and less substrate residue, which greatly simplifies the downstream isolation and purification processes.

DETAILED DESCRIPTION

Materials and Methods:

Assay for Determination of Arginine Deiminase Activity:

The principle of the assay: the activity of arginine deiminase is determined by the citrulline conversion from L-arginine. There is a good linear relationship between the enzyme activity and citrulline concentrations in solutions containing 0-20 mg/L citrulline. The carbamido group of citrulline reacts with diacetylmonoxime (DAM) under acid conditions and condensates to form red oxadiazole compounds, which is detected by a colorimetric method.

Method for enzyme activity determination: dissolve L-arginine in 0.2 M phosphate buffer, pH 6.5 to prepare a 0.2 M L-arginine solution. Mix 1.8 ml L-arginine solution and 0.2 ml enzyme solution to react under 37° C. for 10 min. Dilute the resulting solution for 200-2000 times, and mix 2 ml diluted solution with 3 ml iron-acid solution and 0.5 ml mixed solution of diacetylmonoxime and aminothiourea. Shake the mixture and immediately put it a boiling water bath for 10 min, followed by determining the absorbance at the wavelength of 530 nm.

Preparation of the mixed solution of diacetylmonoxime and aminothiourea: dissolve 1 g diacetylmonoxime and 60 mg aminothiourea in 100 ml water.

Preparation of the iron-acid solution: concentrated phosphoric acid 70 ml, concentrated sulfuric acid 160 ml and 5 ml 10 mg/ml $FeCl_3$ are dissolved in water to obtain a solution with a final volume of 1000 ml.

Determination of L-arginine and L-citrulline By Chromatography:
(a) chromatographic column: Agilent TC-C18 column 250 mm×4.6 mm×5 μm;
(b) column temperature: 40° C.;
(c) mobile phase: preparation of phase A: 8 g sodium acetate is dissolved in 1000 ml water, 225 ml triethylamine is then added, and the pH of the mixture is adjusted to 7.20±0.05 using 5% acetic acid. 5 ml tetrahydrofuran is then added and mixed. Preparation of phase B: 12 g sodium acetate is dissolved in 400 ml water. The pH of the solution is adjusted to 7.20±0.05 by 5% acetic acid, and the resulting solution is mixed with 800 ml acetonitrile and 800 ml of methanol.
(d) detector: the wavelength of the UV detector is 338 nm.

EXAMPLE 1

Primer Design for Cloning of Arginine Deiminase Gene

The forward primer F and the backward primer R for cloning an arginine deiminase gene were designed according to the arcA gene sequence of *Lactobacillus brevis* disclosed by NCBI GenBank database.

Primer F (SEQ ID NO: 2):
5'-ACCCG AAGCTT ATGACAAGTCCGATTCACGTAATG-3' (HindIII)

Primer R (SEQ ID NO: 3):
5'-ACCG GAATTC TTAAAGGTCTTCTCGAACTAATGGC-3' (EcoRI)

EXAMPLE 2

Cloning of the Arginine Deiminase Gene

The genome DNA of *Lactobacillus brevis* was used as a template for cloning the arginine deiminase gene. The primers designed in Example 1 were used for the PCR amplification. The PCR amplification conditions were: 5 min at 94° C.; 35 cycles of 1 min at 94° C., 1 min, at 56° C., 1 min at 72° C.; and 10 min at 72° C. PCR systems was carried out in a 50 μl reaction containing: 1 μl DNA template, 0.4 μl each forward and backward primers, 4 μl dNTP Mix, 5 μL 10×ExTaq Buffer, 37 μl of sterile double distilled water, and 1 μl ExTaq DNA polymerase. The resulting product was purified by a gel extraction kit, and preserved in a 1.5 ml EP at −20° C. for further use. The purified PCR product was ligated to pMD18-T cloning vector, and transformed to *E. coli* JM109 cells. The resulting cells were plated on a LB medium with Ampicillin and incubated at 37° C. overnight. The resulting colonies were picked and transferred to 10 ml liquid LB medium, and incubated at 37° C. overnight. The DNA of the cultured bacteria were extracted and verified by sequencing. The plasmids containing the correct arginine deiminase gene were named as pMD18-T-arcA, and conserved in 15%-20% (w/v) glycerol at −70° C.

EXAMPLE 3

Construction of Recombinant Plasmid pXMJ19-arcA

The recombinant plasmid pMD18-T-arcA and the pXMJ19 were digested by EcoRI and HindIII. The resulting DNA fragment were purified by a gel extraction kit and ligated in a 10 μl ligation system containing 1 μl digestion product from pXMJ19, 7 μl digestion product from pMD18-T-arcA, 1 μl T4 DNA ligase buffer, and 1 μl T4 DNA ligase. The ligation was performed under 16° C. for overnight. The ligated recombinant plasmid pXMJ9-arcA was transformed into *E. coli* JM 109 competent cells, and incubated in LB culture medium containing chloroamphenical for 10 hr. The positive colonies were picked and transferred to 10 ml LB liquid medium. After incubated at 37° C. for overnight, the plasmid was extracted and named as pXMJ9-arcA. After the sequence verification, the correct plasmid pXMJ9-arcA was preserved in 15%-20% (w/v) glycerol at −70° C.

EXAMPLE 4

Construction of Recombinant *C. crenatum* SDNN 403/pXMJ9-arcA

Competent preparation: *C. crenatum* SDNN403 were picked and inoculated into a 10 ml LBG (LB+0.5% glucose) medium, and incubated at 30° C. overnight. 500 μl culture broth were transferred into 50 ml LB medium containing 3% glycine and 0.1% Tween-80 to make the initial cell concentration at 0.3 ($OD_{600}$ value), and then incubated at 30° C., 200 r/min until $OD_{600}$ reached 0.9. The culture was cooled for 15 min after the fermentation finished, the culture was then centrifuged and washed for 4 times using precooled 10% glycerol. After that, the cells were dispensed in 0.2 ml 10% glycerol, and the resulting cell suspension was conserved at 80 μl/1.5 ml EP tube.

Electrotransformation: the electrotransformation was carried out at 1800V for 5 ms. The resulting cell suspension was transferred to 800 μl LBG medium and incubated at 30° C. for 2-3 hr.

The harvest of recombinant C. crenatum SDNN 403/pXMJ9-arcA: the electrotransformed cells were plated on LGB medium containing chloramphenicol, and incubated at 30° C. Positive colonies were picked, and the plasmid DNAs of the picked colonies were extracted and verified by sequencing. The correct colony was named recombinant C. crenatum SDNN403/pXMJ19-arcA.

EXAMPLE 5

Determination of Arginine Deiminase Activity in Recombinant C. crenatum SDNN403/pXMJ19-arcA The recombinant C. crenatum SDNN403/pXMJ19-arcA was inoculated into LBG medium containing 10 ml chloramphenicol, incubated at 30° C. overnight, and then transferred at 1% inoculation rate to 50 ml LBG medium. The cells were incubated at 30° C. for 8 hr until the $OD_{600}$ reached to 0.9. The cells were then added with 0.7 mmol/L (final concentration) IPTG and incubated at 30° C. for 8 hr. The cells were harvested by centrifugation at 10000 rpm for 10 min, and then washed by Tris-HCl buffer for 3 times before resuspended in 5 ml Tris-HCl buffer (pH7.0). The cell suspension was sonicated to obtain the crude enzyme preparation.

The C. crenatum SDNN403 was used as control and treated according to the same procedure above.

1.8 ml 0.2 M L-arginine (pH 6.4, dissolved in 0.2 M phosphate buffer) and 0.2 ml crude enzyme solution was mixed and incubated at 37° C. for 10 min. The resulting solution was diluted to 200-2000-fold, and 2 ml diluted reaction solution was mixed with 3 ml iron-acid solution and 0.5 ml mixed solution of diacetylmonoxime and aminothiourea. The mixed solution was then immediately incubated in a boiling water bath for 10 min, followed by the determination of absorbance values at the wavelength of 530 nm.

Result showed that the arginine deiminase produced by recombinant C. crenatum SDNN403/pXMJ19-arcA was 2.56 U/mg cell mass, while no arginine deiminase activity was detected in C. crenatum SDNN 403.

EXAMPLE 6

Methods for L-citrulline Production Using Whole-cell Biocatalysts

The recombinant C. crenatum SDNN403/pXMJ19-arcA cells were inoculated in 200 ml ADI-producing medium (g/L: glucose, 40; yeast extract 8; $KH_2PO_4$, 2.5; $K_2HPO_4$, 2.3; $MgSO_4$, 0.5) and cultured for 8 hr. The cells were cultured for another 8 hr with addition of 0.7 mM IPTG for induction of arginine deiminase expression, and the cells were collected by centrifugation.

Cells were washed twice by pH 7.0 Tris-HCl and resuspended in 200 ml 0.2 M phosphate buffer (pH 6.4) containing 100 g/L L-arginine, at a cell concentration at $OD_{600}$=7-8.

The whole-cell catalytic reaction was carried out under different temperatures between 20 to 60° C. (the interval was set to be 5° C.). The results showed that the molar conversion rate was only 45.7% of the maximum rate under the temperature of 20° C. The conversion rate increased when temperature rose from 20 to 45° C. When the temperature was higher than 45° C., the conversion rate reduced sharply as the temperature increases. The conversion rate was only 29.3% of the maximum rate at the temperature of 60° C.

The whole-cell catalytic reaction was carried out under different pHs. An acetate buffer (pH 3.5-5.0), a $Na_2HPO_4$-citric acid buffer (pH 5.0-6.0), a phosphate-buffered saline (pH 6.0-8.0), a Tris-HCl buffer (pH 8.0-9.0), and a carbonate buffer (pH 9.0-10.5) were used as the testing buffer solutions. The results showed that the conversion rate was the relatively high under pH 6.0-7.0 with the conversion rate being the highest at pH 6.4. The conversion rate dropped to 76.3% of the maximum rate at pH 4.0. The conversion efficiency were relatively slow under alkaline conditions, indicating that the conversion reaction favors slightly acidic conditions. Different metal ions were added into whole-cell catalytic reaction system, including 1 mM $Cu^{2+}$, $Ca^{2+}$, $Co^{2+}$, $La^{3+}$, $K^+$, $Fe^{2+}$, $Mg^{2+}$, $Ba^{2+}$, $Mn^{2+}$, $Fe^{3+}$, $Al^{3+}$, $Zn^{2+}$, and $Na^+$. The results showed that supplement of $Mn^{2+}$ and $Mg^{2+}$ ions significantly increased the conversion rate. The conversion rate were increased to 183.2% and 167.4% for $Mn^{2+}$ and $Mg^{2+}$ supplements, respectively. Other metal ions showed less activating effect on the conversion process.

The whole-cell catalytic reaction was carried out in 0.2 mol/L phosphate buffer (pH 6.4) containing 100 g/L L-arginine, 1.0 mM $Mn^{2+}$, and 1.0 mM $Mg^{2+}$ with the recombinant cell concentration of OD600=7-8. The conversion process was performed under a temperature of 45° C. with the L-arginine concentration maintained at 60-100 g/L. After 48 hr conversion, high performance liquid chromatography (HPLC) was used to determine the content of L-arginine and L-citrulline. The results showed that, 301.4 g/L L-citrulline was detected in the resulting solution, indicating a mole conversion rate from L-arginine to L-citrulline was 99.9%.

\*\*\*

While the present invention has been described in some detail for purposes of clarity and understanding, one skilled in the art will appreciate that various changes in form and detail can be made without departing from the true scope of the invention. All figures, tables, appendices, patents, patent applications and publications, referred to above, are hereby incorporated by reference.

What is claimed is:

1. A recombinant *Corynebacterium crenatum* SDNN403 strain with expression of an exogenous arginine deiminase gene, wherein the recombinant *Corynebacterium crenatum* SDNN403 strain is made by the following steps: ligating an arginine deiminase gene arcA to plasmid pXMJ19 to make a pXMJ19-arcA plasmid; and transferring the pXMJ19-arcA plasmid to *Corynebacterium crenatum* SDNN403 to obtain the recombinant *Corynebacterium crenatum* SDNN403 strain with expression of an exogenous arginine deiminase gene wherein the exogenous arginine deiminase gene comprises the sequence of SEQ ID NO:1.

2. A method for L-citrulline production comprises producing L-citrulline in a reaction system that uses L-arginine as a substrate and the recombinant cells of claim 1 as whole-cell biocatalysts.

3. The method of claim 2, wherein said reaction system comprises phosphate buffer at pH 6.0-7.0.

4. The method of claim 2, wherein concentration of the recombinant cells is at $OD_{600}$=7-8 and concentration of L-arginine is 80-100 g/L.

5. The method of claim 2, wherein the reaction system has a temperature of 40-45° C.

6. The method of claim 2, wherein the L-arginine concentration in the reaction system is maintained at 60-100 g/L during the process of L-citrulline production.

7. The method of claim 2, wherein the reaction system contains 1.0 mM $Mn^{2+}$ and/or 1.0 mM $Mg^{2+}$.

8. The method of claim 2, wherein the reaction system initially contains a pH 6.4 phosphate buffer, 100 g/L arginine, 1.0 mM $Mn^{2+}$, and 1.0 mM $Mg^{2+}$; and wherein the production process is performed under 40-45° C. with the concentration of L-arginine maintained at 60-100 g/L.

9. The method of claim 2, wherein the reaction system initially contains 100 g/L L-arginine, 1.0 mM $Mn^{2+}$, and 1.0 mM $Mg^{2+}$; and wherein the production process is performed at 45° C. with the concentration of L-arginine maintained at 60-100 g/L.

\* \* \* \* \*